US00PP12882P2

(12) United States Plant Patent
de Gruyter

(10) Patent No.: US PP12,882 P2
(45) Date of Patent: Aug. 27, 2002

(54) FICUS PLANT NAMED 'GRU FI9801'

(75) Inventor: André Paulus de Gruyter, Rockanje (NL)

(73) Assignee: Vulcan Plants Produktontwikkeling B.V., Rockanje (NL)

( * ) Notice: Subject to any disclaimer, the term of this patent is extended or adjusted under 35 U.S.C. 154(b) by 46 days.

(21) Appl. No.: 09/740,564

(22) Filed: Dec. 20, 2000

(51) Int. Cl.[7] ..... A01H 5/00
(52) U.S. Cl. ..... Plt./211
(58) Field of Search ..... Plt./211

*Primary Examiner*—Bruce R. Campell
*Assistant Examiner*—A Para
(74) *Attorney, Agent, or Firm*—C. A. Whealy

(57) ABSTRACT

A new and distinct cultivar of Ficus plant named 'GRU FI9801' characterized by its upright plant habit; freely branching growth habit; and dark green leaves.

1 Drawing Sheet

BACKGROUND OF THE INVENTION

The present Invention relates to a new and distinct cultivar of Ficus, botanically known as *Ficus sp.*, and hereinafter referred to by the name 'GRU FI9801'.

The new Ficus was discovered by the Inventor in a controlled environment in Rockanje, The Netherlands, in 1997, as a naturally-occurring whole plant mutation of an unidentified selection of *Ficus sp.*, not patented. The new Ficus was observed as a single plant in a group of plants of the parent cultivar. The selection of this plant was based on its unique leaf shape, size and coloration.

Asexual reproduction of the new Ficus by cuttings taken in a controlled environment in Rockanje, The Netherlands, has shown that the unique features of this new Ficus are stable and reproduced true to type in successive generations.

SUMMARY OF THE INVENTION

The new Ficus has not been observed under all possible environmental conditions. The phenotype may vary somewhat with variations in environment such as temperature, daylength, light intensity, nutritional and water status without, however, any variance in genotype.

The following traits have been repeatedly observed and are determined to be the unique characteristics of 'GRU FI9801'. These characteristics in combination distinguish 'GRU FI9801' as a new and distinct cultivar:

1. Upright plant habit.
2. Freely branching growth habit.
3. Dark green leaves.

BRIEF DESCRIPTION OF THE PHOTOGRAPH

The accompanying colored photograph illustrates the overall appearance of the new Ficus. This photograph shows the colors as true as it is reasonably possible to obtain in colored reproductions of this type. Colors in the photograph may differ slightly from the color values cited in the detailed botanical description, which accurately describe the colors of the new Ficus. The photograph comprises a side perspective view of a typical plant of 'GRU FI9801'.

DETAILED BOTANICAL DESCRIPTION

The aforementioned and following observations, measurements and values describe plants grown in a glass-covered greenhouse in Rockanje, The Netherlands, during the summer under conditions which approximate commercial production practices. After the cuttings were rooted, plants were planted in 17-cm containers and grown for about five months with day temperatures about 21 to 27° C. and night temperatures about 19 to 22° C. In the following description, color references are made to The Royal Horticultural Society Colour Chart except where general terms of ordinary dictionary significance are used.

Botanical classification: *Ficus sp.* cultivar 'GRU FI9801'.

Parentage: Naturally-occurring whole plant mutation of an unidentified selection of *Ficus sp.*, not patented.

Propagation:

- *Type.*—By cuttings.
- *Time to initiate roots.*—Summer: About 21 days at 24° C. Winter: About 35 days at 24° C.
- *Time to develop roots.*—Summer: About 28 days at 24° C. Winter: About 42 days at 24° C.
- *Root description.*—Thick, fleshy.

Plant description:

- *Plant form.*—Upright plant habit; triangular. Vigorous; suitable for 19 to 24-cm containers.
- *Crop time.*—To produce a finished plant in a 21-cm container, about 20 weeks are required under summer conditions and about 32 weeks are required under winter conditions.
- *Growth rate.*—About 6 to 10 cm per week.
- *Branching habit.*—Freely branching; about 5 to 10 lateral branches develop per plant; pinching is not required. Branching angle of young branches is about 45 to 60° from vertical; and branching angle of older branches is about 70 to 80° from vertical.
- *Plant height.*—About 1.2 m.
- *Plant width.*—About 40 to 50 cm.
- *Lateral branch description.*—Length: Up to 40 cm. Diameter: About 7 mm. Internode length: About 7.5 to 9 cm. Texture: Covered with dense and velvety pubescence. Color: 137B towards base, 165A towards apex; pubescence, ochre to reddish brown.

Foliage description:

*Arrangement.*—Alternate, single.

*Quantity per lateral branch.*—About 5 to 8.

*Length.*—About 31 to 38 cm.

*Width.*—About 13 to 16 cm.

*Shape.*—Obovate.

*Apex.*—Cuspidate.

*Base.*—Between acute and obtuse.

*Margin.*—Entire and undulate.

*Texture.*—Velvety pubescence on both surfaces.

*Color.*—Young leaves, upper surface: 143A. Young leaves, lower surface: 144A. Fully expanded leaves, upper surface: 136A; venation, 153D. Fully expanded leaves, lower surface: 137B; venation, 145C.

*Petiole.*—Length: About 20 to 50 cm. Diameter: About 5 to 8 mm. Texture: Covered with dense pubescence. Color: Pubescence, ochre to reddish brown.

Flower description:

*Flowers have not been observed on plants of the new Ficus.*

Disease resistance: Plants of the new Ficus have not been observed to be resistant to pathogens common to Ficus.

It is claimed:

1. A new and distinct Ficus plant named 'GRU FI9801', as illustrated and described.

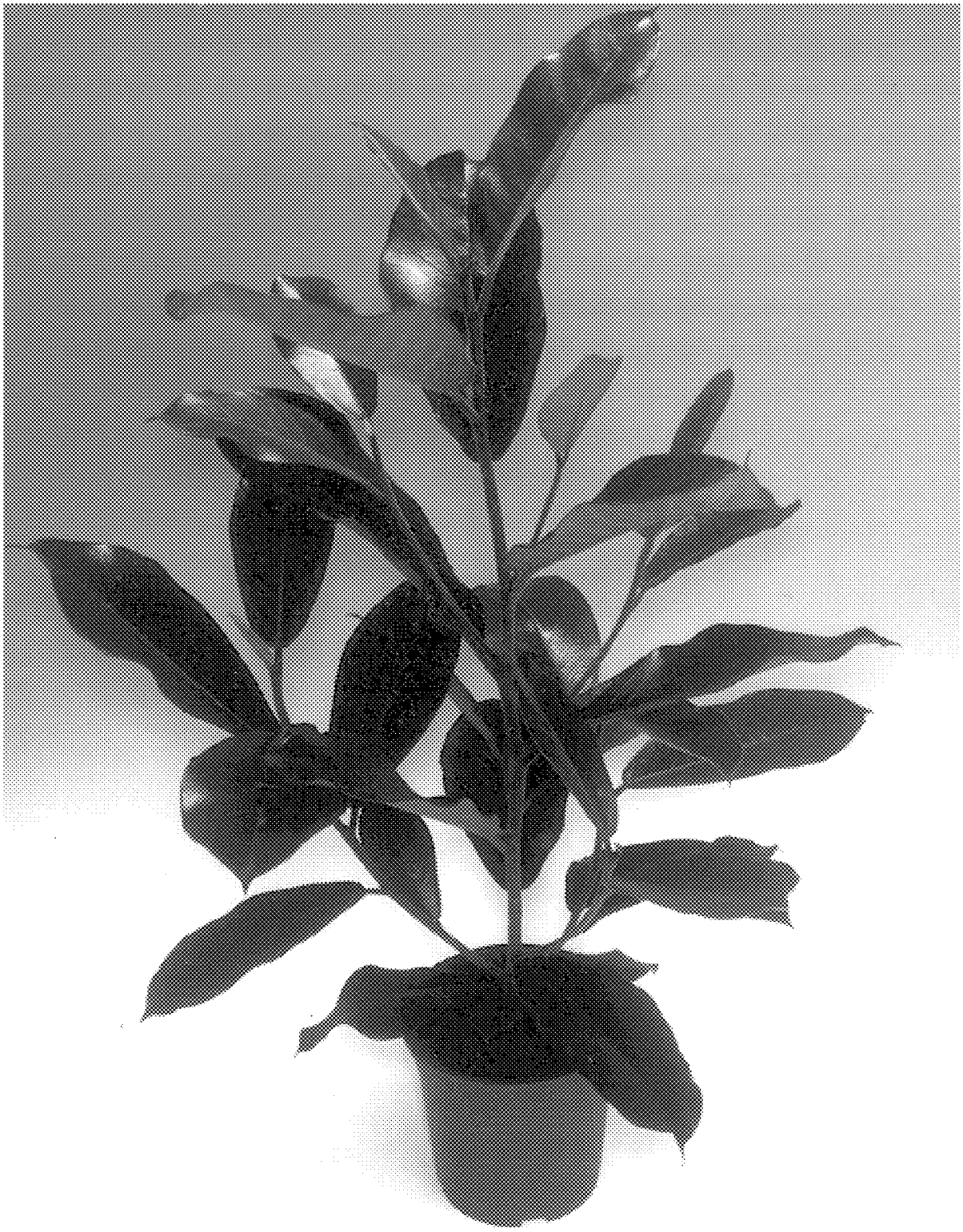

* * * * *